United States Patent [19]

Birchall et al.

[11] 3,974,072
[45] Aug. 10, 1974

[54] FILTRATION METHOD
[75] Inventors: James Derek Birchall; David Cowap; Joseph Park, all of Runcorn, England
[73] Assignee: Imperial Chemical Industries Limited, London, England
[22] Filed: Feb. 25, 1974
[21] Appl. No.: 445,781

[30] Foreign Application Priority Data
Mar. 2, 1973  United Kingdom............... 10237/73

[52] U.S. Cl.................................. 210/65; 106/57; 106/69; 210/167; 210/500 R
[51] Int. Cl.² ........................................ B01D 37/00
[58] Field of Search.................. 210/DIG. 5, 39, 40, 210/41, 64, 65, 50, 52, 167, 500, 502, 503, 508; 264/56, DIG. 19, DIG. 25; 106/57, 65, 69

[56] References Cited
UNITED STATES PATENTS

| | | |
|---|---|---|
| 1,914,999 | 6/1933 | Maverick et al.................... 210/501 |
| 3,224,965 | 12/1965 | Woolery.............................. 210/52 |
| 3,234,075 | 2/1966 | Braitberg........................... 210/64 X |
| 3,507,944 | 4/1970 | Moore, Jr. ............................ 106/57 |
| 3,625,717 | 12/1971 | Grubbe et al......................... 106/65 |
| 3,645,398 | 2/1972 | Flocco ......................... 210/DIG. 5 |
| 3,667,975 | 6/1972 | Teague et al. ........................ 106/65 |
| 3,669,882 | 6/1972 | Hirs .................................... 210/41 |
| 3,709,706 | 1/1973 | Sowman............................... 106/57 |
| 3,732,326 | 5/1973 | Chen.................................... 210/41 |
| 3,738,492 | 6/1973 | Trillich .......................... 210/DIG. 5 |
| 3,764,355 | 10/1973 | Moore, Jr. ............................ 106/65 |

*Primary Examiner*—Theodore A. Granger
*Attorney, Agent, or Firm*—Cushman, Darby & Cushman

[57] ABSTRACT

Microorganisms are removed from cutting-oil emulsions, and their growth is inhibited by passage through a filter comprising an inorganic fiber.

6 Claims, No Drawings

FILTRATION METHOD

This invention relates to filtration, to filters, to the use of such filters and more particularly to the use of such filters for the removal of microorganisms.

The effectiveness of coolants used in the course of metal-working operations such as machining or rolling may be seriously reduced by the growth therein of microorganisms. The said coolants are generally emulsions in which the cooling properties of a water-phase are combined with the lubricant and anti-corrosive properties of an oil-phase. Such emulsions frequently contain the necessary nutrients to provide a culture medium for the growth of microorganisms such as bacteria or, under some conditions, yeasts for fungal spores.

The growth of such microorganisms results in the biodegradation of the oil and the production of unpleasant odours. Furthermore the stability of the emulsion is reduced, and increased corrosion of the workpiece and tools is observed.

At present it is usual to change the coolant frequently, and to add a disinfectant comprising a biocide or biostat.

However the selection of a suitable disinfectant which is compatible with the particular coolant in use requires experimentation, whilst the development of a resistant organism is always a possibility. Furthermore such disinfectants may give rise to dermatitic skin reaction in the machine operators, and are difficult to dispose of satisfactorily after use.

According to the present invention we provide a process for treating cutting oil emulsions infected with microorganisms which comprises passing the said emulsion through a filter comprising a mass of inorganic fibre, whereby the concentration of the said microorganisms is reduced, and the growth of said microorganisms is inhibited.

The term "cutting-oil emulsion" may be taken to include any emulsion comprising an oil-phase, and capable of acting as a coolant or lubricant for a metal working process, including, for example cutting, turning, threading, boring, broaching, drilling, grinding, polishing, rolling or forming. The emulsion commonly comprises an oil-phase and an aqueous-phase, and may be a water-in-oil emulsion or, more commonly, an oil-in-water emulsion.

The emulsion may be treated according to the present invention by a single passage through the filter, but it is preferred to pass the emulsion through the filter more than once, for example by re-circulating the emulsion continuously through the filter during the operation of the metal-working process. If desired a conventional filter (for example a wire mesh filter) may be additionally employed to remove metallic particles from the emulsion.

Passage through the filter removes microorganisms from the emulsion, trapping them within the filter. It is a surprising feature of the present invention that microorganisms thus trapped do not re-infect the emulsion, so that not only is the concentration of microorganisms in the emulsion reduced, but the further growth of such microorganisms is also inhibited, for example by repeated circulation of the emulsion through the filter.

A wide variety of fibres may be used in the process of the present invention. Suitable fibres include, for example asbestos fibre, glass fibre, and aluminosilicate fibre. Especially preferred are synthetic polycrystalline refractory oxide fibres, as such fibres have the diameters and surface properties found to be the most effective for use in the present invention. Mixtures of such fibres may be used if desired.

Synthetic polycrystalline refractory fibres (including, for example zirconia, alumina and alumina/silica fibres) are conveniently prepared by fibrising a sol or solution, preferably an aqueous sol or solution, of salt or other compound convertible to the material of which the fibre consists. Suitable methods are described in U.K. patent specification No. 1,098,595 (U.S. Pat. No. 3,322,865). The said fibres are especially conveniently prepared by methods in which the aforementioned sol or solution comprises additionally a co-dissolved organic polymer, particularly a linear organic polymer. Such methods are described in our co-pending U.K. patent application No. 29909/70-4369/71 (published as Netherlands application No. 7,108,399), the disclosure of which is incorporated herein by reference. In these methods, fibres are formed by fibrising a composition having a viscosity of greater than 1 poise comprising an aqueous solution or sol of a metal compound, for example an oxychloride, basic acetate, basic formate or nitrate of a metal, especially of aluminium and/or zirconium, and a minor proportion of a water-soluble organic polymer, preferably polyethylene oxide, polyvinyl alcohol, or polyvinylpyrrolidone, drying the fibre formed and heating to decompose the metal compound to oxide and to decompose the polymer.

Removal of the microorganisms from the emulsion is facilitated when the filter comprises fine fibres, and it is preferred to employ, for example fibres having a mean diameter below 10 microns. However, filters constructed from extremely fine fibres (such as asbestos) tend to give very slow filtration rates and readily become blocked or blinded. It is therefore expecially preferred to employ fibres having a mean diameter within the range 0.1 to 10 microns, for example from 0.5 to 5 microns.

The effectiveness of a fibre as a filter medium according to the present invention depends on other physical properties in addition to the mean diameter. For example, to achieve uniformity in the internal structure of the filter, it is preferred that the fibre should have a narrow distribution of diameters about the mean diameter, and be substantially free from shot (defined as non-fibrous material having at least one dimension substantially greater than the mean fibre diameter).

It is a particular advantage of synthetic inorganic polycrystalline fibres that their physical characteristics (including, for example diameter, diameter distribution, surface area, porosity, bulk density and freedom from shot) can be more readily and accurately controlled than those of glassy or natural inorganic fibres.

The filter is required to be reasonably robust to withstand the flow of liquids and the pressure difference between its surfaces, and therefore the fibres used therein should not be weak and easily damaged or suffer deterioration in physical properties in use. Furthermore destabilisation of the emulsion during its passage through the filter is undesirable. Small diameter polycrystalline metal oxide fibres, for example alumina or zirconia fibres of 0.5 to 5 micron diameter are relatively very strong inorganic fibres and have surface properties which do not lead to emulsion destabilisation. Such fibres are thus very suitable for the present invention.

Polycrystalline inorganic fibres having the aforementioned desirable characteristics of small and uniform diameter, high surface area, strength and shotfreedom are conveniently produced by a blowing process described in our co-pending U.K. patent application No. 29909/70-4369/71. This process comprises extruding a fibrising composition, for example one of those hereinbefore described, through one or more apertures, preferably 50–500 microns diameter, into at least one gas stream having a component of high velocity in the direction of travel of the extruded composition. It is convenient to use two streams of gas which converge, preferably at an angle of 30° to 60°, at or near the point where the composition is extruded from the aperture so to draw down the fibre. Air is the preferred gas. The rate of removal of water from the composition is conveniently controlled by mixing the gas with water vapour, for example air at a relative humidity of greater than 80% may be used. The fibres are collected as staple in a random mat form, and then fired at 1000° to 2000°C. Alumina, alumina/silica or zirconia fibres suitable for the invention are conveniently made by this process.

The filter may be made up in any convenient form: it may for example comprise fibre which is inserted into a filter defining space. The fibres can be used loose, with exterior support in the form of, for example, one or more metal meshes or perforated plates. Alternatively they can be self-supporting as the result, for example, of bonding by an organic or inorganic binder. Suitable inorganic binders include, for example hydraulic cement or clay or refractory oxide produced from colloidal or dissolved inorganic oxy compounds such as hydrated oxide sols, for example sols of alumina, silica, titania, zirconia and mixtures of two or more of these or decomposable compounds such as alkali metal silicates, organic esters of inorganic acids such as alkyl silicates and alkyl titanates, soluble compounds of aluminium and zirconium and precursors of aluminium phosphate. Suitable organic binders include, for example organic resins (for example phenol formaldehyde resin) and latices (for example an acrylic latex). Since it is desirable to keep up the permeability of the filter element, the concentration of bonding agent must not be too great, and therefore the use of a relatively low concentration of bonding agent in conjunction with an external support is a generally useful arrangement. Unbound fibres are also in general more flexible and thus able to accommodate strains more readily.

The packing density of fibres in the filter element may be varied over wide limits, for example from 0.02 to 0.4g/cc, to give filter elements with porosities in the range 90–99%. Porosities in this range provide filters which retain sufficiently useful amounts of particulate matter without becoming easily blocked.

Packing densities for zirconia fibres preferably lie in the range 0.06 to 0.34g/cc and for alumina fibres preferably in the range 0.03 to 0.27g/cc. A typical packing density for zirconia is substantially 0.25g/cc and for alumina substantially 0.2g/cc.

The fibre used in the invention may be in a variety of forms, for example loose staple, paper, cloth, sheet, board or felt, depending upon the particular design of filter element employed. The fibre forms may be arranged in a wide variety of geometrical structures. Use of the fibres in paper form (prepared, for example as described in our co-pending British patent application No. 33917/73) provides the opportunity of presenting a very large filtration area to the emulsion; in such cases the thickness of the filtration layer is relatively small so that low pressure drop is achieved. However cylinders, plugs or wads of fibre may also be used in which the filtration area presented to the liquid is relatively small.

The filter element may for example take the form of a loosely-wound spiral roll comprising two or more layers of a paper of similar width prepared from the fibres in which pairs of adjacent edges on both sides of the roll are joined in liquid-tight manner, and in which the joins on one side alternate with the joins on the other side, for example as described in British patent specification No. 693,495. Liquid flowing in an axial direction through the roll is thereby filtered and a large filtration area contained in a relatively compact space. The paper is preferably corrugated or creped to maintain a sufficient gap between adjacent layers of paper to allow free-flow of the liquid.

The filter element may also, for example take the form of a hollow cylinder of the fibrous material in loose or bound form. Such a cylinder is conveniently made by spiral or helical winding of a yarn, paper or felt of the fibre on to a tubular mandrel, which may be removed or more conveniently left in place to serve as a permanent support for the fibres as hereinafter described, in which case it is perforated to allow liquid to come into contact with the fibres. In using such hollow cylindrical filter elements one end of the cylinder is closed and the liquid is normally led to the inside of the cylinder and taken away from the outside surface of the cylinder. The cylinder may be contained within, and supported by, foraminous materials (for example perforated metal or plastics plate or wire-mesh), placed in contact with its curved surfaces.

The filter may comprise a mixture of inorganic fibres, for example a mixture of alumina, alumina/silica or zirconia fibre with one or more fibres including, for example asbestos, glass and aluminosilicate fibres. The filter may additionally comprise organic fibres, for example cellulose, nylon or polyethylene fibres. the relative proportions of the fibres comprising the filter may be varied within wide limits.

Particulate fillers or adsorbants (including, for example kieselguhr, active carbons, fullers earth, polyvinyl pyrrolidone and nylon) may also be added to the filter.

It is an advantage of inorganic fibres when used according to the present invention that filters constructed therefrom may be sterilised (for example by heating or by treatment with steam) either before or after use. Furthermore organic matter trapped within a filter constructed from the said fibres may be removed (for example by subjecting the filter to heat in the presence of air, and the filter re-used.

It is a particular advantage of synthetic inorganic refractory oxide fibres when used in the present invention that the fibres may be treated at a sufficiently high temperature to destroy and burn off all organic matter, including for example spores.

The invention is illustrated by the following Examples:

EXAMPLE 1

A filter element comprising zirconia fibre (having fibre diameters within the range 1 to 5 microns) was introduced into the cutting oil circuit of a conventional lathe. The cutting oil circuit consisted of a pump delivering fluid to the working area and a sump of capacity 30 litres to which the fluid was returned. The fluid was 3% by weight of Shell Dromus 80 oil emulsified in water, and was circulated at a rate of 50 ml per second. The filter was introduced into the circuit between the pump and the delivery head.

The filter element comprised 50g of zirconia fibre in the form of a blanket of bulk density 10 pounds per cubic foot of material. The blanket was cylindrically wound thereby forming a cylinder of 5 cm diameter × 15 cm long. The cylinder was protected at one end by a wire wool plug and supported at the other by a gauze. The whole element was enclosed in a plastic cylindrical container so as to provide a filter chamber having an inlet and an outlet with the filter element or media intermediate said inlet and outlet.

At the time the filter was installed the cutting fluid was already contaminated though not odorous. Within a short space of time its appearance actually improved and the experiment was continued unattended for seven weeks. During this time the emulsion retained its stability and no unpleasant odours developed. It was not necessary to add disinfectant.

By way of comparison the same lathe was operated without a filter. To maintain the cutting oil emulsion in an acceptable condition it proved necessary to renew the emulsion every three months, and to add disinfectant every two weeks.

EXAMPLE 2

10 litres of a cutting-oil emulsion comprising 3% by weight of Shell Dromus BS cutting oil emulsified in water was circulated in a circuit comprising a reservoir, pump, filter housing and flow and pressure measurement devices. A filter element to be enclosed within the filter housing comprised 50g of alumina fibre (commercially available under the trade mark "Saffil") in the form of a felt. The felt was cylindrically wound on to a cylindrical, perforated mandril and the element thus formed was enclosed in a cylindrical perforated container. Annular members perpendicular to the cylinder axis enclosed the fibre within the filter element thus formed. The emulsion was passed through the outer, cylindrical, perforated container, and flowed radially through the fibre and the inner, perforated mandrel. The emulsion flowed out of the filter element axially along the cylindrical mandrel.

2 ml of a sample of cutting-oil emulsion infected with bacteria comprising Pseudomonas spp and Nocardia spp was added to the 10 litres of emulsion to give a very low concentration of bacteria in the emulsion. To build up the concentration of bacteria, and by way of comparison, the emulsion was circulated through the circuit with no filter element in the filter housing. The pump was operated to circulate the emulsion for a period of 8 hours each day, the pump being switched off and the emulsion being static within the circuit for the remaining 16 hours. After 3 days the concentration of bacteria had increased to $10^7$ per ml.

The filter element was now replaced in the filter housing, and the same daily cycle of 8 hours' circulation of emulsion followed by a period of 16 hours static rest was continued for 10 days. During this period the concentration of bacteria in the emulsion fell to $10^2$ per ml. No changes in the cutting-oil emulsion were observed and no fungal contamination could be detected.

The flow-rate of the emulsion remained virtually constant at approximately 150 litres/hour throughout the period. The pressure drop across the filter similarly remained virtually constant at approximately 20 cm of water.

What we claim is:

1. In a metal working operation including a circuit for recirculating a cutting oil emulsion wherein the cutting oil emulsion contains microorganisms, a process for removing the microorganisms from the cutting oil emulsion recirculated in said circuit by filtering, said process comprising the steps of:

providing a filter chamber with an inlet and an outlet, locating within said chamber intermediate said inlet and said outlet a filter medium comprising fibers of at least one inorganic polycrystalline refractory oxide selected from the group consisting of zirconia, alumina and silica, introducing used cutting oil emulsion containing microorganisms into the inlet of said chamber for filtering by said filtering medium, and recirculating the cutting oil emulsion discharged from the outlet of said chamber for reuse in said metal working operation, whereby microorganisms which were contained in said cutting oil emulsion are separated therefrom and prevented from recombining with said emulsion by being retained on said filter medium within said chamber.

2. A process as claimed in claim 1 where said fibers have a mean diameter of 0.1 to 10 microns.

3. A process as claimed in claim 1 wherein the emulsion is an oil-in-water emulsion.

4. A process as claimed in claim 1 wherein the fibers comprise alumina.

5. A process as claimed in claim 1 wherein the fibers comprise zirconia.

6. A process as claimed in claim 1 wherein the fiber diameter is from 0.5 to 5 microns.

* * * * *